United States Patent [19]

Kito et al.

[11] Patent Number: 5,328,681
[45] Date of Patent: Jul. 12, 1994

[54] COMPOSITION COMPRISING MAGNETIC METAL OXIDE ULTRAFINE PARTICLES AND DERIVATIZED POLYSACCHARIDES

[75] Inventors: Kyoji Kito, Nagoya; Hideo Nagae, Kasugai; Masakatsu Hasegawa, Nagoya; Yoshio Ito, Nagoya; Akihiro Mizutani, Nagoya; Kimio Hirose, Gifu; Yasuji Yamashita, Nagoya; Nahoko Tozawa, Seto; Keiko Yamada, Ogaki; Masahiro Ohgai, Nagoya; Shusaburo Hokukoku, Kani, all of Japan

[73] Assignee: Meito Sangyo Kabushiki Kaisha, Nagoya, Japan

[21] Appl. No.: 934,637

[22] PCT Filed: Jan. 17, 1992

[86] PCT No.: PCT/JP92/00031
§ 371 Date: Sep. 17, 1992
§ 102(e) Date: Sep. 17, 1992

[87] PCT Pub. No.: WO92/12735
PCT Pub. Date: Aug. 6, 1992

[30] Foreign Application Priority Data

Jan. 19, 1991 [JP] Japan .................. 3-019512

[51] Int. Cl.⁵ .................. A61B 5/055; A61K 37/10; A61K 31/715

[52] U.S. Cl. .................. 424/9; 424/5; 424/646; 424/648; 436/173; 436/806; 423/633; 128/653.4; 514/8; 514/54; 514/57; 514/60

[58] Field of Search .................. 424/9, 5, 646, 648; 436/173, 806; 423/633; 128/653.4, 654; 514/8, 54, 57, 60

[56] References Cited

U.S. PATENT DOCUMENTS

| | | | |
|---|---|---|---|
| 4,663,166 | 5/1987 | Veech | 424/146 |
| 4,795,698 | 1/1989 | Owen et al. | 435/4 |
| 5,102,652 | 4/1992 | Groman et al. | 424/9 |
| 5,160,726 | 11/1992 | Josephson et al. | 424/9 |

Primary Examiner—Gary E. Hollinden
Attorney, Agent, or Firm—Wenderoth, Lind & Ponack

[57] ABSTRACT

A composition containing magnetic metal oxide ultrafine particles, which comprises an aqueous sol of a complex of the magnetic metal oxide ultrafine particles with a polysaccharide, a polysaccharide derivative and/or a protein; and an organic monocarboxylic acid. The composition is free of side effects such as platelet aggregation, is safe for use with living bodies, and, in the case of intravascular administration, has no harmful effects on living bodies, and is useful in fields such as medicine and diagnostic drugs.

21 Claims, 3 Drawing Sheets

FIG. 1(A)   FIG. 1(B)
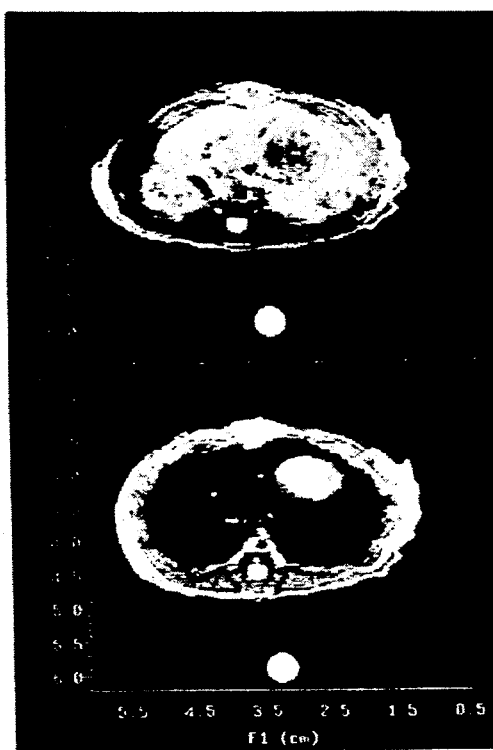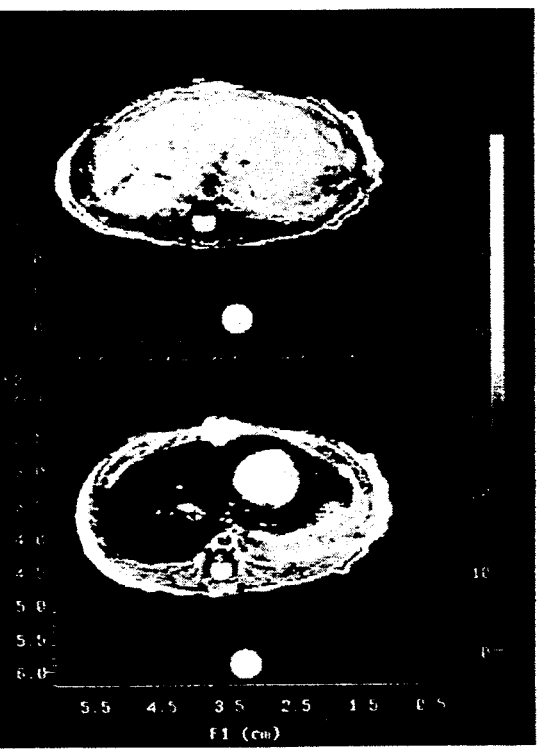
FIG. 1(C)   FIG. 1(D)

COMPOSITION COMPRISING MAGNETIC METAL OXIDE ULTRAFINE PARTICLES AND DERIVATIZED POLYSACCHARIDES

TECHNICAL FIELD

This invention relates to a composition containing ultrafine particles of a magnetic metal oxide, which is useful in the fields of medicine and diagnostic drugs, especially as an MRI contrast agent.

BACKGROUND ART

A composition comprising magnetic metal oxide ultrafine particles, for example, so-called magnetic fluid, has various uses, and there can be mentioned, as one field thereof, a use as a base for diagnostic drugs.

However, in order to safely and efficaciously administer to living organisms metal oxide fine particles of macromolecular size, various factors must be considered. Known preparations have various drawbacks, particularly problems are recognized in the point of biocompatibility, and various proposals are made for improvement. For example, Japanese Tokuhyosho 500196/1989 (PCT/WO88/00060) discloses dextran-coated superparamagnetic fluid dispersed in a polycarboxylic acid buffer. For use of these magnetic fluid preparations in the medical field, some points including toxicity should still be improved.

In the application of magnetic fluid to medicine and diagnostic drugs, particularly as a result of research on the aspect of its toxicity, the present inventors found that magnetic fluid as a foreign substance within living bodies has a bad influence on living bodies, for example, it aggregates platelets which are an important constituent of blood, and this is a cause of toxicity of magnetic fluid.

Thus, the present inventors intensely studied aiming to develop a magnetic fluid which is free of side effects such as platelet aggregation, is excellent in safety to living bodies, and, when intravascularly administered, does not have a bad influence on living bodies. As a result, we have found that when an organic monocarboxylic acid, e.g. lactic acid is compounded into an aqueous sol of a complex of magnetic metal oxide ultrafine particles with a polysaccharide, a polysaccharide derivative and/or a protein, the property of the aqueous sol to aggregate platelets can remarkably be reduced without substantial change in the intrinsic properties of the aqueous sol such as magnetic properties, metabolic properties and tissue specificity, and completed this invention.

DISCLOSURE OF INVENTION

Thus, this invention provides a magnetic metal oxide ultrafine particles-containing composition which comprises an aqueous sol of a complex of magnetic metal oxide ultrafine particles with a polysaccharide, a polysaccharide derivative and/or a protein; and an organic monocarboxylic acid.

The magnetic metal oxide ultrafine particles-containing composition provided by this invention has only weak toxicity; hardly shows any blood pressure lowering effect, which is different from the case of usual magnetic fluids, even when directly administered into blood vessels of animals; and moreover, has only a very small platelet aggregating action and therefore, is excellent in safety as a drug, and can, for example, be used as a MRI contrast agent, a hyperthermic agent or a carrier for drug delivery.

BRIEF DESCRIPTION OF DRAWINGS

FIG. 1 is a MR image of the liver site of a Wistar strain rat into whose liver Novikoff tumor was implanted. In FIG. 1, (1A) and (1B) are MR images before administration of the complex sol preparation of this invention prepared in the later-described Example 10, and (1C) and (1D) are MR images at 60 minutes after administration of the preparation. Although the tumor portion cannot be recognized at all in (1A) and (1B), the shape and size of the tumor part can clearly be recognized in (C) and (D).

DETAILED DESCRIPTION OF THE INVENTION

Figure 2A:
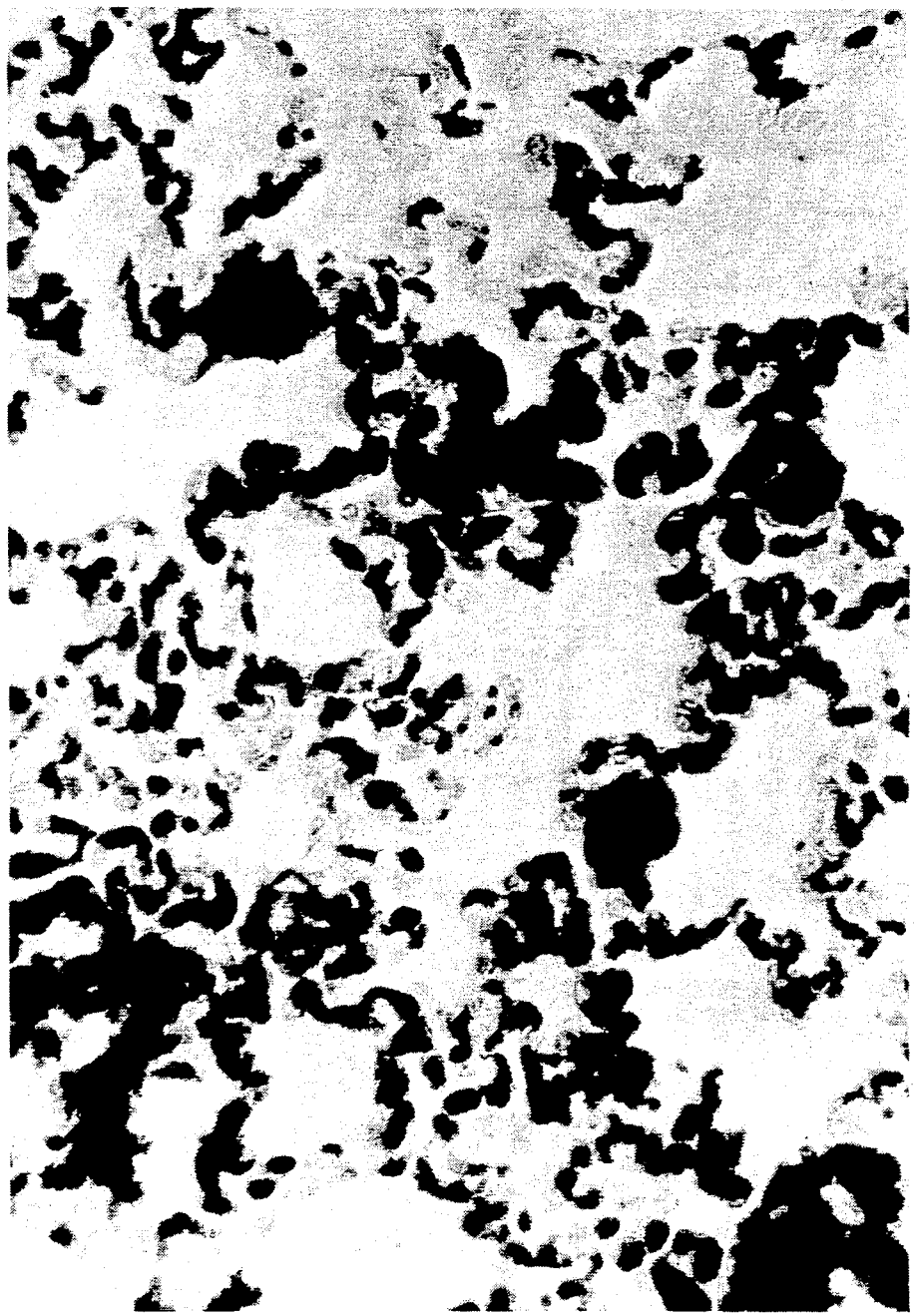
FIG. 2 (A) and (B) are photomicrographs of the lungs of dd-strain mice to which the complex aqueous sol preparation prepared in the later-described Comparative example 1 and Example 2-3 were administered, respectively. Although marked emboli are observed in the lung in Photograph (2A) (Comparative example 1), no embolus is observed in the lung in photograph (2B) (Example 2-3).

The composition of this invention is described in more detail below.

The complex, as one component which forms the composition of this invention, of magnetic metal oxide ultrafine particles with a polysaccharide, a polysaccharide derivative (hereinafter, polysaccharide and polysaccharide derivative together are abbreviated as polysaccharides) and/or a protein is at least partially known, and can be prepared, for example, by a method which comprises reacting a previously prepared aqueous sol of magnetic metal oxide ultrafine particles with polysaccharides and/or a protein (hereafter referred to as the first method), or by a method which comprises forming magnetic metal oxide ultrafine particles in the presence of polysaccharides and/or a protein (hereinafter referred to as the second method), or the like.

As magnetic metal oxides forming magnetic metal oxide ultrafine particles, there can be exemplified those represented by the following formula

$$(M^{II}O)_l \cdot M_2^{III}O_3 \qquad (I)$$

wherein $M^{II}$ represents a divalent metal atom, $M^{III}$ represents a trivalent metal atom and $l$ is a number in the range of $0 \leq l \leq 1$. In the formula (I), examples of the divalent metal atom $M^{II}$ are magnesium, calcium, manganese, iron, nickel, cobalt, copper, zinc, strontium, barium, etc., and they can be used alone or in combination of two or more. Further, examples of the trivalent metal atom $M^{III}$ are aluminum, iron, yttrium, neodymium, samarium, europium, gadolinium, etc., and they can be used alone or in combination of two or more of them.

Preferred are magnetic metal oxides wherein $M^{III}$ in the formula (I) is a trivalent iron, namely ferrites represented by the following formula

$$(M^{II}O)_m \cdot Fe_2O_3 \qquad (II)$$

wherein $M^{II}$ is as defined above and $m$ is a number in the range of $0 \leq m \leq 1$. As $M^{II}$, there can be mentioned the same metals as exemplified in the above formula (I). Particularly, the magnetic metal oxides of the formula (II) wherein $M^{II}$ is divalent iron, namely magnetic iron oxides represented by the following formula $$(FeO)_n \cdot Fe_2O_3 \quad (III)$$

wherein n is a number in the range of $0 \leq n \leq 1$, can also be mentioned as further preferred magnetic metal oxides in this invention. In the formula (III), the case of $n=0$ shows $\gamma$-iron oxide ($\gamma$-Fe$_2$O$_3$) and the case of $n=1$ shows magnetite (Fe$_3$O$_4$).

Preferred among them in this invention are magnetic iron oxides whose divalent iron content is 10 weight % or less, particularly about 2 to about 7 weight %.

Further, it is also possible to use, as magnetic metal oxides in this invention, magnetic metal oxides represented by the following formula $$M^{II}M^{IV}O_3 \quad (IV)$$

and $$M^{IV}O_2 \quad (V)$$

wherein $M^{II}$ represents a divalent metal atom and $M^{IV}$ represents a tetravalent metal atom. As the divalent metal atoms $M^{II}$, there can be exemplified those described above, and as the tetravalent metal atoms $M^{IV}$, there can, for example, be mentioned vanadium, chromium, manganese, etc.

Specific examples of the magnetic metal oxides represented by the formula (IV) or (V) are, for example, NiMnO$_3$, CoMnO$_3$, CrO$_2$, etc. The magnetic metal oxides in this invention include magnetic metal oxides having water of crystallization, too.

Further, as polysaccharides being capable of forming complexes with the above magnetic metal oxide ultrafine particles, water soluble ones are preferred, and examples of the polysaccharide are glucose polymers such as dextran, starch, glycogen, pullulan, curdlan, schizophyllan and pestalotian; fructose polymers such as inulin and levan; mannose polymers such as mannan; galactose polymers such as agarose and galactan; xylose polymers such as xylan; L-arabinose polymers such as arabinan; etc., and examples of the polysaccharide derivative are modified polysaccharides obtained by heat treating the above polysaccharide with an alkali such as sodium hydroxide (i.e., carboxy polysaccharide); carboxyalkyl ethers of the above polysaccharides or cellulose; etc. Further, as the proteins, there can be exemplified water soluble proteins such as, for example, albumin and globulin.

Preferred in this invention are the polysaccharides and polysaccharide derivatives. Among them, preferred as the polysaccharide is dextran, and preferred as the polysaccharide derivatives are alkali-modified derivatives of dextran, starch and pullulan (carboxy polysaccharides), and carboxy lower alkyl-etherified derivatives thereof, especially carboxymethyldextran. The intrinsic viscosity of the polysaccharides can be in the range of generally about 0.02 to about 0.5 dl/g, preferably about 0.04 to 0.2 dl/g.

In the first method for preparation of the complex of this invention, an aqueous sol of magnetic metal oxide ultrafine particles is first prepared. An alkali coprecipitation method, an ion exchange resin method or the like can be exemplified as a preparation method for the aqueous sol. The alkali coprecipitation method comprises, for example, mixing a 0.1 to 2M aqueous solution containing a divalent metal salt, preferably a divalent iron salt and a trivalent metal salt, preferably a trivalent iron salt in a mole ratio of 1:3 to 2:1, with a base such as NaOH, KOH or NH$_4$OH so that the pH is in the range of 7 to 12; if necessary, heating and aging; after separation and water washing of the magnetic metal oxide precipitated, redispersing the magnetic metal oxide in water; and adding a mineral acid such as hydrochloric acid until the pH of the liquid is in the range of 1 to 3 to obtain a magnetic metal oxide aqueous sol. On the other hand, the ion exchange method comprises, for example, adding a 0.1 to 2M aqueous solution containing a ferrous salt and a ferric salt in a mole ratio of about 1:2 to a slurry of a strongly basic ion exchange resin under stirring while maintaining the pH in the range of 8 to 9; adding a mineral acid such as hydrochloric acid until the pH of the liquid becomes 1 to 3; and filtering out the resin to obtain a magnetic iron oxide aqueous sol.

If necessary, these aqueous sols can be purified and/or concentrated by dialysis, ultrafiltration, centrifugation, etc.

The magnetic metal oxide aqueous sol thus obtained and a polysaccharides and/or protein aqueous solution were mixed such that the weight ratio of the magnetic metal oxide to the polysaccharides and/or protein is in the range of about 1:1 to about 1:6 in terms of the metal(s), and the reaction is carried out with heating. The concentration of the magnetic metal oxide in the reaction solution is not particularly limited, but can be in the range of usually 0.1 to 10 W/V %, preferably 1 to 5 W/V % as metal. The reaction can generally be carried out at a temperature in the range of room temperature to 120° C. for about 10 minutes to 10 hours, but usually, it is sufficient to carry out reflux with heating for about 1 hour. Then, purification, etc. can be carried out by method(s) known per se. For example, a complex aqueous sol having the desired purity and concentration can be obtained by repeating an operation to separate the unreacted polysaccharides and/or protein and low molecular weight compounds from the formed complex by ultrafiltration; or a complex aqueous sol can be obtained by adding to the resultant reaction solution a poor solvent for the complex such as methanol, ethanol or acetone to precipitate and deposit the complex preferentially, separating the deposit, redissolving the deposit in water, dialyzing the resultant solution against flowing water, and if necessary, concentrating the inner solution under reduced pressure; or a complex aqueous sol having the desired purity and concentration can be obtained by passing the resultant reaction solution through a gel filtration column, and if necessary, concentrating the resulting solution under reduced pressure. In this method, it is also possible, if desired, to add steps of pH adjustment, centrifugation and/or filtration in the course of and/or at the last of the above steps.

The second method for preparation of the complex in this invention is a method of obtaining the complex by one step, which comprises mixing and reacting, in the presence of polysaccharides and/or a protein, an aqueous mixed metal salt solution containing a divalent metal salt, preferably a divalent iron salt and a trivalent metal salt, preferably a trivalent iron salt with a aqueous base solution. This second method can further be classified, according to addition order, into (A) a method which comprises adding the aqueous mixed metal salt solution to an aqueous polysaccharides and/or protein solution, and then adding the aqueous base solution to carry out reaction; (B) a method which comprises adding the aqueous base solution to the aqueous polysaccharides and/or protein solution, and then adding the aqueous mixed metal salt solution to carry out reaction; (C) a method which comprises adding to the aqueous base solution a mixed solution of the aqueous polysaccharides and/or protein solution with the aqueous mixed metal salt solution; (D) a method which comprises adding to the aqueous mixed metal salt solution a mixed solution of the aqueous polysaccharides and/or protein solution with the aqueous base solution; etc.

These methods (A), (B), (C) and (D) are mutually different only in addition order, and other reaction conditions are not essentially different from one another.

Preparation of the above aqueous mixed metal salt solution can be carried out by dissolving in an aqueous medium a divalent metal salt, preferably a divalent iron salt and a trivalent metal salt, preferably a trivalent iron salt in a mole ratio of about 1:4 to about 3:1, preferably about 1:3 to about 1:1. The concentration of this aqueous metal salt solution can be varied over a wide range, but is suitably in the range of usually about 0.1 to about 3M, preferably about 0.5 to about 2M.

As the metal salts, there can, for example, be mentioned salts with mineral acids such as hydrochloric acid, sulfuric acid and nitric acid, and as the bases, there can, for example, be used at least one selected from alkali metal hydroxides such as NaOH and KOH; amines such as ammonia, triethylamine and trimethylamine; and the like. The concentration of the aqueous base solution can be varied over a wide range, too, but is suitable in the range of usually about 0.1 to about 10N, preferably about 1 to about 5N. The quantity of the base used can be such a quantity that the pH of the reaction solution after completion of the addition falls into the range of around neutrality to about 12, namely such a quantity that the ratio of the metal salt to the base becomes about 1:1 to about 1:1.5 (normal ratio).

Further, the quantity of the polysaccharides and/or protein used can be about 1-fold to about 15-fold, preferably about 3-fold to about 10-fold the weight of the metal(s) in the metal salt. Further, the concentration of the aqueous polysaccharides and/or protein solution is not strictly limited, either, but is suitable in the range of usually about 1 to about 40 W/V %, preferably about 5 to 30 W/V %. Addition of each aqueous solution and mixing can be carried out with stirring at room temperature to about 100° C. with heating, and after pH adjustment, when needed, with addition of a base or acid, reaction is carried out at a temperature of about 30° to about 120° C. for about 10 minutes to about 5 hours, usually by refluxing the mixture with heating for about 1 hour. The resultant reaction solution can be purified in the same manner as in the above first method, and if desired, subjected to pH adjustment, concentration and further filtration.

As the complexes in this invention, there can likewise be used, besides those prepared as above, for example, a complex of dextran or modified dextran obtained by heat treating dextran with sodium hydroxide (namely, carboxydextran—hereafter sometimes abbreviated as CDX) with a magnetic iron oxide having a particle size of 3 to 20 nm, disclosed in Japanese Patent Publication No. 13521/1984 (U.S. Pat. No. 4,101,435); magnetic iron-dextran microspheres of molecular complex structure comprising magnetic iron oxide particles having a colloidal diameter coated with dextran molecules, disclosed in U.S. Pat. No. 4,452,773; complex microspheres comprising magnetic iron oxide particles having a colloidal diameter coated with dextran molecules or protein molecules, disclosed in Japanese Tokuhyosho 500196/1989 (PCT/WO88/00060); carboxyalkylated polysaccharides and magnetic metal oxides having a particle size of 2 to 30 nm, disclosed in Japanese Patent Application No. 271784/1989 (PCT/JP90/01346); etc.

Further, in this invention, when the magnetic metal oxide in the complex obtained as above is a magnetic iron oxide, it is further preferred that it is an oxidized magnetic iron oxide, of only a small content of divalent iron, preferably whose divalent iron content is 10 weight % or less of the whole iron in terms of iron metal, and polysaccharides, particularly dextran and/or carboxydextran are preferred as complex stabilizers of magnetic iron oxide particles. Such a complex of polysaccharides with magnetic iron oxide (hereafter sometimes abbreviated as a complex oxide) can be prepared by making a suitable oxidizing agent act on an aqueous sol of a complex prepared by the first or second method, preferably the second method. The oxidizing agent used therefor is preferably an oxidizing agent which oxidizes magnetic iron oxide to reduce the divalent iron content but does not substantially oxidize nor decompose polysaccharides, and there can, for example, be exemplified peroxides such as hydrogen peroxide, oxidizing gases such as oxygen gas and a mixed gas of oxygen gas with an inert gas.

First, in oxidation with peroxide, hydrogen peroxide, ozone, etc. can be exemplified as peroxides used, but hydrogen peroxide is preferred. Although the concentration of the raw material complex aqueous sol in the oxidation reaction is not particularly limited, it can be in the range of generally about 0.1 to about 4M, preferably about 0.5 to about 2M as iron. Peroxide is added to this aqueous sol in a quantity of about 0.5 to about 10-fold, preferably about 1 to about 5-fold that of the latter in a mole ratio to divalent iron. The reaction is carried out, preferably with stirring, at a temperature of about 0° to about 80° C., preferably about 15 to about 40° C. for about 10 minutes to about 24 hours, preferably about 1 to about 5 hours. If desired, after addition of a decomposing agent of peroxide such as sodium sulfite, purification, etc. are carried out in the same way as in the case of the above complex to obtain an iron oxide complex aqueous sol of this invention having the desired purity, concentration and pH. In this instance, particularly when purification is carried out by an ultrafiltration method, the polysaccharides content of the complex becomes too small wherein, it is preferred for enhancement of stability to add the polysaccharides up to the desired concentration. The particle diameter of the whole iron oxide complex obtained is somewhat smaller than that of the raw material complex and generally about 70% to the same extent, the particle diameter of the magnetic iron oxide in the complex oxide is almost the same with that of the raw material complex, and the magnetization of the resultant oxidized complex in 1 tesla is generally 80% to the same extent compared to that of the raw material complex.

On the other hand, in case of oxidation with oxidizing gas, there can be exemplified, as a usable oxidizing gas, oxygen gas or a mixed gas of an inert gas such as nitrogen gas, argon gas or helium gas with oxygen gas, but oxygen gas is particularly preferred. In the oxidation reaction with the oxidizing gas, the concentration of the complex aqueous sol is not particularly limited, either, and can be in the range of about 0.1 to about 4M, preferably about 0.5 to about 2M as above. Reaction can be carried out in an atmosphere of oxidizing gas, if desired under increasing pressure, with heating at a temperature of room temperature to about 120° C., preferably about 60° to about 100° C., with such adjustment that the final pH is about 3 to about 8, preferably about 4 to about 6, for about 0.5 hour to about 3 days, preferably about 2 to about 16 hours. Then, if necessary, purification, etc. are carried out in the same way as in the above method to obtain a complex oxide aqueous sol for use in this invention having the desired purity, concentration and pH. In this method, particularly when purification is carried out by an ultrafiltration method wherein, the polysaccharide content of the complex becomes too small, it is likewise preferred to add the polysaccharides until the desired concentration is attained. Oxidizing gas, particularly oxygen gas is preferred from the viewpoint that side reactions take place to a smaller extent compared to the case where peroxide was used. The properties of the resultant complex oxide show the same change tendency as in the case where peroxide was used.

In this invention, in complexes obtained by any of the methods, the ratio of the polysaccharides and/or protein to the magnetic metal oxide ultrafine particles depends on the diameter of the magnetic metal oxide ultrafine particles and/or the molecular weight of the protein, etc., and can be varied over a wide range, but it is generally suitable that the complex contains the polysaccharides and/or the protein in the range of about 0.1 to about 5 weight parts, preferably about 0.3 to about 2 weight parts per weight of the metal(s) in the magnetic metal oxide.

The metal content of the complex in this invention (all the metals deriving from the magnetic metal oxide are contained in this metal) is evaluated according to the method disclosed in item 17 atomic absorption spectrophotometry in The Pharmacopoeia of Japan (the 11th revision, 1986). Namely, the metal content is determined by adding concentrated hydrochloric acid to an aqueous sol or powder of the complex, completely changing the metal oxide(s) into metal chloride(s), suitably diluting the mixture, and comparing the dilution with a standard solution of each metal.

Further, the polysaccharides content of the complex is evaluated by a sulfuric acid-anthrone method according to Analytical Chem., 25, 1656 (1953). Namely, a dilution obtained by suitably diluting the hydrochloric acid-decomposed solution used in measurement of the above metal content is added to sulfuric acid-anthrone reagent to develop color, and then absorbance is measured. At the same time, the same color development and measurement of absorbance as above are made using as a standard substance the polysaccharides used in preparation of the complex, and the content of the polysaccharides is determined based on the ratio of both absorbances. On the other hand, the protein content of the complex is evaluated according to a general test method, the method disclosed in item 26 nitrogen determination method in The Pharmacopoeia of Japan (the 11th revision, 1986). Namely, the nitrogen content is determined on the complex and the protein used for preparation thereof, and the protein content is determined from the ratio of both.

Further, in this invention, it is preferred to use a complex comprising magnetic iron oxide, and in this case, a oxidized complex comprising polysaccharides and magnetic iron oxide is particularly preferred, and it is particularly preferred that its divalent iron content is about 10 weight % or less, preferably about 2 to about 7 weight % of the whole iron in terms of iron metal. The extent of oxidation of the complex oxide can be expressed by divalent iron content, and the divalent iron content can be determined by a colorimetric determination method using o-phenanthroline. Namely, under sufficient consideration for prevention of oxidation during measurement such as replacement with nitrogen, hydrochloric acid is added to an aqueous sol or powder of the complex, and after completely changing of the iron oxide to iron chlorides, the mixture is suitably diluted to give a test solution. To 1 ml of this test solution are added 8 ml of 0.1% o-phenanthroline reagent solution in 0.4M acetate buffer (pH 4) and then 1 ml of 1M potassium fluoride, and absorbance is measured at a wavelength of 510 nm. On the other hand, absorbance is likewise measured on the divalent iron standard solution and water used for the measurement, and the divalent iron content is determined from their ratio.

Further, in this invention, the average diameter of the magnetic metal oxide ultrafine particles in the complex used can be in the range of generally about 2 to about 30 nm, preferably about 4 to about 15 nm. In this specification, the particle diameter of magnetic metal oxide ultrafine particles is a value determined by an X-ray diffraction method. Namely, when X-ray diffraction is carried out on powders of a raw material complex and the composition of this invention freeze-dried, several diffraction peaks corresponding to particular compounds can be observed, and thus it is seen that the magnetic metal oxide (magnetic particles) contained in the complex exists in a crystal form. The diffraction peak obtained becomes broader, i.e. smaller in proportion to the decrease of the diameter of the magnetic particles contained in the complex. Therefore, in case the particle size of the magnetic metal oxide contained in the complex is 0.1 μm or less, the particle size can be measured by X-ray diffraction. Namely, the particle size (diameter) can be calculated according to the following Scherrer equation based on the strongest peak in an X-ray diffraction.

$$D = k\lambda/\beta \cdot \cos\theta,$$

$$\beta = \sqrt{B^2 - b^2}$$

wherein D is particle size (Å), k is a constant 0.9, λ is an X-ray wavelength (1.790 Å), θ is Bragg's angle (degree), B is the half width of a sample (radian) and b is the half width of a standard sample (radian).

The standard sample used is the same substance having a particle size of 1 μm or more. The values thus obtained are in comparatively good accordance with the values obtained by a transmission type electron microscope.

Further, in this invention, the particle diameter of a complex itself is a value measured by a light scattering method [for example, refer to Polymer J., 13, 1037–1043 (1981)], and complexes used in this invention can have a particle diameter in the range of generally about 10 to about 500 nm, preferably about 20 to about 200 nm.

Further, in this description, magnetic properties of a complex (for example, magnetization and coercive force) can be determined from a magnetization-magnetic field curve (so-called M-H curve) drawn using a vibrating sample magnetometer. The magnetization in 1 tesla of a complex used in this invention can be in the range of generally about 10 to about 150 emu, preferably about 30 to about 150 emu per g of the metal(s). Further, the coercive force of a complex usable in this invention can be about 30 oersteds or less, and preferably, it is substantially superparamagnetic.

Further, in this description, the $T_2$ relaxivity [unit: $(sec.mM)^{-1}$] of the composition of this invention and/or its raw material complex can be determined from the gradient of a straight line determined by the method of least squares based on a graph obtained by drawing resonance curves of the proton of water on aqueous sols comprising each complex diluted with water into various concentrations and on water used for dilution, using CW-NMR of 60 MHz (magnetic field is about 1.4 tesla), determining the half width $\Delta\nu_{\frac{1}{2}}$ (unit: Hz) of the resultant peak, calculating $1/T_2$ (unit: $sec^{-1}$)=$\pi.\Delta\nu_{\frac{1}{2}}$, and plotting the relation between $1/T_2$ and the iron concentration (unit: mM) in the measurement sample aqueous sol. The $T_2$ relaxivity of a raw material complex usable in this invention calculated as above can be in the range of generally about 5 to about 1000 $(sec.mM)^{-1}$, preferably about 10 to about 500 $(sec.mM)^{-1}$, more preferably about 20 to about 300 $(sec.mM)^{-1}$.

The thus described aqueous sol of a magnetic metal oxide ultrafine particles-polysaccharides and/or protein complex, preferably a magnetic metal oxide ultrafine particles-polysaccharides complex can be mixed with an organic monocarboxylic acid to give the composition of this invention. In this method, although such a composition can be prepared by adding and mixing an aqueous sol of the complex to and with an aqueous organic monocarboxylic acid solution such as a lactic acid Ringer's solution, it is usually convenient to prepare it by adding an organic monocarboxylic acid or an aqueous solution thereof to an aqueous sol of the complex. Further, in some case, it can also be prepared by removing impurities contained in an aqueous sol of the complex and at the same time incorporating an organic monocarboxylic acid, according to an ultrafiltration method or dialysis method.

The concentration of the complex aqueous sol used is not strictly limited, but can be in the range of generally about 0.05 to about 6M, preferably about 0.2 to about 2M in terms of metal(s), and its pH is suitably in the range of about 4 to about 10, preferably about 5 to about 9. It is possible to mix such a monocarboxylic acid with the complex aqueous sol in the range of about 1 mmol to about 30 mol, preferably about 5 mmol to about 100 mmol per mol of the metal(s) in the complex. An organic monocarboxylic acid used can be added in a form of a salt with a monovalent cation such as lithium, sodium, potassium, ammonia or a lower alkylamine, or a divalent cation such as magnesium, calcium or barium, preferably sodium, but more preferably is added in a free acid form. The concentration of the aqueous organic monocarboxylic acid solution at the time of addition is not particularly limited, either, but can, for example, be generally about 0.01M or more, preferably in the range of about 0.2 to about 2M.

In this invention, monocarboxylic acids capable of being added are preferably water soluble, and in this case monocarboxylic acids being in a free acid form and water soluble are preferred, but water soluble monocarboxylic acid salts can be used, too. As such water soluble monocarboxylic acids, those having 10 or less carbon atoms are preferred, and further, monocarboxylic acids having hydroxyl group(s) and/or amino group(s) can suitably be used, too. Specific examples of organic monocarboxylic acids suitably usable in this invention are as follows.

(i) Fatty acids: for example, acetic acid, propionic acid, butyric acid, isobutyric acid, valeric acid, isovaleric acid, methylethylacetic acid, trimethylacetic acid, tert-butylacetic acid, caproic acid, diethylacetic acid, heptanoic acid, caprylic acid, valproic acid, nonanoic acid, etc.

(ii) Organic monocarboxylic acids containing hydroxyl group(s): for example, glycolic acid, 3-hydroxypropionic acid, lactic acid, $\beta$-hydroxybutyric acid, 4-hydroxybutyric acid, glyceric acid, mevalonic acid, gluconic acid, gulonic acid, glycoheptoic acid, etc.

(iii) Organic monocarboxylic acids containing amine group(s): for example, glycine, alanine, $\alpha$-aminobutyric acid, valine, norvaline, leucine, norleucine, isoleucine, phenylalanine, tyrosine, surinamine, threonine, serine, proline, oxyproline, tryptophan, thyroxine, diiodotyrosine, dibromotyrosine, methionine, cystine, cysteine, lysine, arginine, hystidine, $\beta$-alanine, $\beta$-aminobutyric acid, $\gamma$-aminobutyric acid, $\delta$-aminovaleric acid, etc. Further, although aspartic acid, glutamic acid, $\beta$-oxyglutamic acid, etc. are dicarboxylic acids, they can be used in this invention, equally to monocarboxylic acids, since they have an amino group, too.

(iv) Ketone acids: for example, pyruvic acid, acetoacetic acid, levulinic acid, etc.

These organic monocarboxylic acids can respectively be used alone or in combination of two or more. Preferred among these organic monocarboxylic acids are lower aliphatic monocarboxylic acids having 6 or less carbon atoms which optionally have hydroxyl group(s) or amino group(s), and lactic acid is particularly preferred.

Although the pH of a mixture of the complex aqueous sol with the organic monocarboxylic acid is not particularly limited, it is suitable that the pH is in the range of generally about 4 to about 11, preferably about 5 to about 9, more preferably about 6 to about 8. Further, the composition of this invention can be subjected to concentration adjustment and filtration, if desired, and further subjected to heat treatment, if desired. It is suitable to carry out the heat treatment generally at a temperature of about 60° to about 140° C. for about 5 minutes to about 5 hours, and particularly, including sterilization, at 121° C. for 20 to 30 minutes.

It is also possible, if desired, to add, before or after the heat treatment, for example, as isotonizing agents, inorganic salts such as sodium chloride, monosaccharides such as glucose, or sugar alcohols such as mannitol or sorbitol; or as pH-holding agents, various physiologically acceptable auxiliaries such as phosphate buffers or Tris buffers. Further, the composition of this invention, irrespective of containing or not containing these auxiliaries, can be powdered by a method known per se, preferably a freeze-drying method, and the resultant powder becomes aqueous sol with addition of water.

The composition of this invention thus obtained comes not to have a hypotensive action and/or show a platelet aggregating action, compared to the complex used as a raw material, but there is not much change on chemical, physical or other biological properties. That is, an extremely preferred effect is brought about in that the safety of the composition of this invention increases, and an effect, e.g., as a MRI contrast agent, acute toxicity, etc. do not change. Heretofore, a composition comprising a polycarboxylic acid such as citric acid and a complex similar to that used in this invention has already been proposed, and in this composition with a polycarboxylic acid side effects such as blood pressure lowering and a platelet aggregating action are undoubtedly reduced, but the composition has a serious drawback of strong acute toxicity. On the other hand, the composition of the present invention containing a monocarboxylic acid has only weak acute toxicity. For example, the $LD_{50}$ values of the complexes of Example 2-3 as a preferred embodiment of this invention, Comparative example 1 and Reference example 4 as the raw material of them are 28 mmol Fe/kg, 9 mmol Fe/kg and 22 mmol Fe/kg, and the composition of this invention containing a monocarboxylic acid is extremely useful as medicine or a diagnostic drug.

Figure 2:

Further, for example when the composition of this invention is administered to an animal and histopathological examination is made on its lung, embolus is not observed as is demonstrated in the later-described Test example 4 [refer to FIG. 2 (B)], and thus the composition has extremely high safety.

The composition of this invention exhibits only a weak hypotensive action. In the present description, blood pressure measurement is made by intravenously administering to each rabbit a complex aqueous sol such as the composition of this invention, for example in a quantity of 0.2 mmol/kg as the metal(s). When it has a hypotensive action, blood pressure lowering is observed generally in the range of about 2 to about 10 minutes after the administration. The composition of this invention has a hypotensive action weaker than that of the complex aqueous sol used as its raw material. For example, the composition of Example 1 as a preferred embodiment of this invention does not exhibit a hypotensive action, but the complex aqueous sol of Reference example 2 as its raw material exhibits a hypotensive action.

Further, the composition of this invention exhibits only a weak platelet aggregating action. In the present description, the aggregating property of platelet is expressed by residual platelet. Namely, a complex aqueous sol such as the composition of this invention is intravenously administered to a rabbit, for example in a quantity of 0.1 mmol/kg as the metal(s), and the ratio of platelet number at 5 minutes after the administration to platelet number immediately before the administration is designated residual platelet (%). Complex aqueous sols used as raw materials in this invention generally exhibit residual platelets of about 1 to about 50%, whereas the composition of this invention generally exhibit residual platelets enhanced about 2 to about 10 times. For example, the residual platelets of the complexes of Example 1 as a preferred embodiment of this invention and Reference example 2 as its raw material are 38 and 3%, respectively, and further, the residual platelets of the complexes of Example 2-3, Comparative example 1 and Reference example 4 as their raw materials are 102, 97 and 56%, respectively.

It was found that at least the magnetic particle part of the complex in each complex aqueous sol included in the composition of this invention tends to accumulate, promptly after intravenous administration, in internal organs where the reticuloendothelial system is developed, for example, liver, spleen and bone marrow, and particularly, in a low dose (for example, 0.1 mmol/kg as the metal(s)), the majority, probably substantially all of the complex administered accumulates at the stellate cell of Kupffer in the liver. Based on this fact, the metabolic properties of these complexes were evaluated as follows by measuring the degree of magnetization of the livers using CW-NMR.

Portions of each of the complex aqueous sols are intravenously administered, respectively, to rats in a quantity of 0.1 mmol/kg each as the metal(s); $1/T_2$ (unit: $sec^{-1}$) values are determined in the same manner as in measurement of $T_2$ relaxivity on the liver of each rat at the time when, for example, 1 hour, 2 hours, 4 hours, 1 day, 3 days, 7 days and 14 days passed after the administration; and after making corrections by the $1/T_2$ values of the livers of the nonadministered rat group, the metabolic property of each complex is calculated as its half life from the relation with times after the administration. The half life of the composition shows in a preferred embodiment of this invention, for example Example 2-3 is 3.6 days, whereas that of the raw material complex shown in Reference example 4 is 3.9 days, and thus it can be said that the metabolic property of the composition is rather better than that of the raw material complex.

Further, physical properties with respect to the composition of this invention such as the particle diameter of the magnetic metal oxide, and the particle diameter, magnetic properties and $T_2$ relaxivity fall in the range of about 80 to about 120% of those of the complex used as a raw material, respectively, and thus hardly change.

The composition of this invention has various excellent characteristics stated above, and can be used safely in the biological field and the medical field, for example as an iron-supplementing agent, an X-ray contrast agent and a MRI contrast agent, for measurement of bloodstream, as a hyperthermic agent, and further as a carrier in case of intensive administration of a drug to a topical part utilizing magnetic field, etc., and among them, can particularly advantageously be used in uses to administer it into blood vessels.

The composition of this invention preferably usable as a MRI contrast agent is a preferred embodiment of this invention. In this preferred embodiment, as the polysaccharides and/or protein forming the complex aqueous sol, as one component of the composition of this invention, polysaccharides, particularly dextran, starch or pullulan are preferred, and, above all, a carboxy polysaccharide or a carboxyalkyl ether of a polysaccharide is preferred. The intrinsic viscosities of these polysaccharides can be in the range of about 0.02 to about 0.5 dl/g, preferably about 0.04 to about 0.2 dl/g. On the other hand, the magnetic metal oxide is preferably magnetic iron oxide, more preferably oxidation treated magnetic iron oxide, the particle diameter of this magnetic metal oxide can be in the range of about 2 to about 30 nm, preferably about 4 to about 15 nm, and the most preferred combination is a complex or oxidized complex of CDX with a magnetic iron oxide. Further, it is desirable that the magnetization of a complex usable for the composition of this invention per 1 g of the metal(s) in 1 tesla is in the range of about 10 to about 150 emu, preferably about 30 to about 150 emu, and it is suitable that the $T_2$ relaxivity of the complex is in the range of generally about 5 to about 1000 $(sec.mM)^{-1}$, preferably about 10 to about 500 $(sec.mM)^{-1}$, preferably about 20 to about 300 $(sec.mM)^{-1}$.

Further, in the composition of this invention preferably usable as a MRI contrast agent, as an organic monocarboxylic acid compoundable into the above complex aqueous sol, lactic acid is particularly preferred among those described above.

Further, when the composition of this invention is used as a MRI contrast agent, it is desirable to use the composition as a form of an aqueous sol. In this regard, the concentration of the complex in the composition can be varied over a wide range, but usually can, for example, be in the range of about 1 1 mmol/l to about 4 mol/l, preferably about 0.01 to about 2 mol/l in terms of the metal(s). Further, in preparation of aqueous sols, there can also be added various physiologically acceptable additives, for example, inorganic salts such as sodium chloride, monosaccharides such as glucose, sugar alcohols such as mannitol or sorbitol, phosphate buffers, Tris buffers, etc. The dose of the composition of this invention when used as a MRI contrast agent varies depending on diagnostic sites and cannot be described definitely, but usually, is in the range of about 1 $\mu$mol/kg to about 10 mmol/kg body weight, preferably about 2 $\mu$mol/kg to about 1 mmol/kg body weight. As administration methods, there can, for example, be mentioned intravenous, intraarterial, intravesical, intramuscular, subcutaneous, intracutaneous, etc. injection, and so on, but in some case oral administration or direct administration into bowels is also possible. For example, when the composition of this invention in a preferred embodiment is intravenously administered, most of it gathers in the reticuloendothelial system, particularly the liver, comparatively promptly, for example within tens of minutes to several hours, and as a result MRI photographs of the liver are suitably made. In this method when there is in the liver a lesion part such as, for example, cancer which lacks reticuloendothelial system cells or has only a small distribution thereof, none or only a smaller part of the complex contained in the composition of this invention gathers at the lesion part, compared to other normal parts, and thus specification of the lesion part by MRI photograph can easily be carried out [refer to the later-described Test example 3 and FIG. 1 (A) to (D)]. The composition of this invention has effects as a contrast agent against not only $T_2$ images but $T_1$ images.

BEST MODE OF CARRYING OUT THE INVENTION

This invention is more specifically described below according to examples.

Reference Example 1

105 g of dextran having an intrinsic viscosity of 0.051 dl/g is dissolved in 350 ml of water, to this is added an aqueous solution comprising 140 ml of 1M aqueous ferric chloride solution (corresponding to 37.8 g of ferric chloride hexahydrate) having dissolved therein 27.2 g of ferrous chloride tetrahydrate under a nitrogen stream, and, with further heating, 305 ml of 3N aqueous sodium hydroxide solution is added under stirring. Then, 6N hydrochloric acid is added to adjust the pH to 7.0 and the mixture is refluxed with heating for 1 hour and 30 minutes. After cooling, centrifugation is made at 2,100×g for 30 minutes, 92.8% of the supernatant volume of ethanol is added thereto to precipitate a complex, the precipitate obtained is dissolved in water, and the solution is dialyzed against flowing water for 16 hours. The dialyzed solution is adjusted to pH 7.2 with sodium hydroxide, concentrated under reduced pressure, and filtered with a membrane filter (pore size: 0.2 $\mu$m) to obtain 40 ml of a desired complex aqueous sol (Reference example 1). Iron concentration: 144 mg/ml, particle size of the magnetic iron oxide: 6.2 nm, particle size of the whole: 89 nm, polysaccharide/iron weight ratio: 0.63, magnetization in 1 tesla: 64 emu/1 g iron, $T_2$ relaxivity: 130 $(mM.sec)^{-1}$, divalent iron rate in the whole iron: 21%.

Reference Example 2

105 g of CDX having an intrinsic viscosity of 0.050 dl/g is dissolved in 350 ml of water, to this is added an aqueous solution comprising 140 ml of 1M aqueous ferric chloride solution (corresponding to 37.8 g of ferric chloride hexahydrate) having dissolved therein 13.6 g of ferrous chloride tetrahydrate under a nitrogen stream, and, with heating, 242 ml of 3N aqueous sodium hydroxide solution is added under stirring. Then, 6N hydrochloric acid is added to adjust the pH to 7.0, and the mixture is refluxed with heating for 1 hour and 30 minutes. After cooling, the same treatment as in Reference example 1 is carried out to obtain 190 ml of a desired complex aqueous sol (Reference example 2). Iron concentration: 56 mg/ml, particle size of the magnetic iron oxide: 8.8 nm, particle size of the whole: 70 nm, polysaccharide/iron weight ratio: 1.08, magnetization in 1 tesla: 91 emu/1 g iron, $T_2$ relaxivity: 230 $(mM.sec)^{-1}$, divalent iron rate in the whole iron: 21%.

Reference Example 3

1,050 g of CDX having an intrinsic viscosity of 0.050 dl/g is dissolved in 3,500 ml of water, to this is added an aqueous solution comprising 1,400 ml of 1M aqueous ferric chloride solution (corresponding to 378 g of ferric chloride hexahydrate) having dissolved therein 136 g of ferrous chloride tetrahydrate under a nitrogen stream, and, with heating, 2,420 ml of 3N aqueous sodium hydroxide solution is added under stirring. Then, 6N hydrochloric acid is added to adjust the pH to 7.1, and the mixture is refluxed with heating for 2 hours. After cooling, centrifugation is made at 2,100×g for 30 minutes, the supernatant is filtered with a membrane filter (pore size: 0.2 $\mu$m), water is added to the filtrate to 10 l, concentration by ultrafiltration (fractional molecular weight: 100,000 daltons) is carried out to 1.5 l, and while water is added to the concentrate, ultrafiltration (fractional molecular weight: 100,000 daltons) is carried out until the quantity of the ejected solution becomes 12 l. A predetermined quantity of CDX is added to the filtration inner solution so that the weight ratio of CDX to iron becomes 1:1, the pH is adjusted to 7.0 with sodium hydroxide, centrifugation is carried out at 2,100×g for 1 hour and 30 minutes, and the supernatant is filtered with a membrane filter (pore size: 0.2 $\mu$m) to obtain 1.9 l of a desired complex aqueous sol (Reference example 3). Iron concentration: 57 mg/ml, particle size of the magnetic iron oxide: 8.6 nm, particle size of the whole: 64 nm, polysaccharide/iron weight ratio: 1.03, magnetization in 1 tesla: 89 emu/1 g iron, $T_2$ relaxivity: 220 $(mM.sec)^{-1}$, divalent iron rate in the whole iron: 23%.

Reference Example 4

According to Reference example 3, 1,050 g of CDX having an intrinsic viscosity of 0.050 dl/g is dissolved in 3,500 ml of water, to this is added an aqueous solution comprising 1,400 ml of 1M aqueous ferric chloride solution (corresponding to 378 g of ferric chloride hexahydrate) having dissolved therein 136 g of ferrous chloride tetrahydrate under a nitrogen stream, and, with heating, 2,420 ml of 3N aqueous sodium hydroxide solution is added under stirring. Then, 6N hydrochloric acid is added to adjust the pH to 7.1, and the mixture is refluxed with heating for 2 hours. After cooling, concentration is made at 2,100×g for 30 minutes, the supernatant is filtered with a membrane filter (pore size: 0.2 μm), water is added to the filtrate to 10 l, concentration by ultrafiltration (fractional molecular weight: 100,000 daltons) is carried out to 1.5 l, and while water is added to the concentrate, ultrafiltration (fractional molecular weight: 100,000 daltons) is carried out until the quantity of the ejected solution becomes 1.5 l. 1.9 l of the resultant complex aqueous sol of CDX having an intrinsic viscosity of 0.050 dl/g with the magnetic iron oxide (iron concentration: 57 mg/ml) wherein the weight ratio of CDX with iron is 0.4:1 is adjusted to pH 7.5 with sodium hydroxide, and oxidation is carried out with oxygen gas at 95° C. for 3 hours and 30 minutes, while the reaction pH is adjusted with sodium hydroxide not to become 4.2 or less. After cooling, the reaction solution is concentrated by ultrafiltration (fractional molecular weight: 100,000 daltons) to 1 l, and while water is added to the concentrate, ultrafiltration (fractional molecular weight: 100,000 daltons) is carried out until the quantity of the ejected solution becomes 12 l. A predetermined quantity of CDX is added to the filtration inner solution so that the weight ratio of CDX to iron becomes 1:1, the pH is adjusted to 7.0 with sodium hydroxide, centrifugation is carried out, and the supernatant is filtered with a membrane filter (pore size: 0.2 μm) to obtain 1.75 l of a desired complex aqueous sol (Reference example 4). Iron concentration: 56 mg/ml, particle size of the magnetic iron oxide: 8.5 nm, particle size of the whole: 67 nm, polysaccharide/iron weight ratio: 1.08, magnetization in 1 tesla: 87 emu/1g iron, $T_2$ relaxivity: 210 $(mM.sec)^{-1}$, divalent iron rate in the whole iron: 3.4%.

Reference Example 5

167 g of CDX having an intrinsic viscosity of 0.120 dl/g is dissolved in 700 ml of water, to this is added an aqueous solution comprising 280 ml of 1M aqueous ferric chloride solution (corresponding to 75.6 g of ferric chloride hexahydrate) having dissolved therein 27.2 g of ferrous chloride tetrahydrate under a nitrogen stream, and, with heating, 484 ml of 3N aqueous sodium hydroxide solution is added under stirring. Then, 6N hydrochloric acid is added to adjust the pH to 7.0, and the mixture is refluxed with heating for 1 hours and 30 minutes. After cooling, centrifugation is made at 2,100×g for 30 minutes, ethanol is added in a quantity of 54.9% of the volume of the supernatant to precipitate a complex, and centrifugation is carried out at 2,100×g for 10 minutes. The resultant precipitate is dissolved in water, ethanol is added in a quantity of 57.1% of the volume of the solution to reprecipitate the complex, centrifugation is carried out at 2,100×g for 10 minutes, the resultant precipitate is dissolved in water, and the solution is dialyzed against flowing water for 16 hours. The dialyzed solution is adjusted to pH 7.2 with sodium hydroxide, concentrated under reduced pressure, and filtered with a membrane filter (pore size: 0.2 μm) to obtain 390 ml of a magnetic iron oxide complex aqueous sol (iron concentration: 56 mg/ml). 300 ml of this complex aqueous sol (iron concentration: 56 mg/ml) is oxidized with oxygen gas at 95° C. for 3 hours and 30 minutes in the same manner as in Reference example 4, and, after cooling, dialyzed against flowing water for 16 hours. The dialyzed solution is adjusted to pH 7.2 with sodium hydroxide, concentrated under reduced pressure, and filtered with a membrane filter (pore size: 0.2 μm) to obtain 285 ml of a desired complex aqueous sol (Reference example 5). Iron concentration: 55 mg/ml, particle size of the magnetic iron oxide: 7.7 nm, particle size of the whole: 78 nm, polysaccharide substance/iron weight ratio: 0.97, magnetization in 1 tesla: 84 emu/1 g iron, $T_2$ relaxivity: 205 $(mM.sec)^{-1}$, divalent iron rate in the whole iron: 1.7%.

Reference Example 6

To a mixed solution of 50 ml of 1M zinc sulfate with 150 ml of 0.5M ferric sulfate is dropwise added under stirring with heating 210 ml of 3N aqueous sodium hydroxide solution, and the mixture is refluxed with heating for 3 hours. After cooling, an operation of centrifuging the reaction mixture and water washing the precipitate with 450 ml of water is repeated four times in total. To the resultant suspension of a ferrite (liquid volume: 300 ml) is added about 2.5 ml of concentrated hydrochloric acid to adjust the pH to 1.7, and the mixture is stirred for 16 hours. To 300 ml of the resultant ferrite aqueous sol (pH 2.1) is added a solution comprising 90 ml of water having dissolved therein 45 g of CDX having an intrinsic viscosity of 0.120 dl/g, and the mixture is adjusted to pH about 7 with sodium hydroxide and then refluxed with heating for 1 hour. After cooling methanol is added to this reaction solution up to 46%, the deposited precipitate is dissolved in 150 ml of water, then, centrifugation is carried out at 2,100×g for 30 minutes, and an aqueous sol of a complex obtained by removal of the precipitate is dialyzed against flowing water for 16 hours. The dialyzed solution is adjusted to pH 8.0 with sodium hydroxide, concentrated under reduced pressure, and filtered with a membrane filter (pore size: 0.45 μm) to obtain 168 ml of a desired complex aqueous sol (Reference example 6). Iron concentration: 42 mg/ml, zinc concentration: 16 mg/ml, particle size of the magnetic metal: 10.3 nm, particle size of the whole: 120 nm, polysaccharide metal weight ratio: 1.33, magnetization in 1 tesla: 27 emu/1 g metal, $T_2$ relaxivity: 22 $(mM.sec)^{-1}$.

Reference Example 7

86 g of sodium salt of carboxymethylated dextran (intrinsic viscosity: 0.115 dl/g, degree of substitution: 0.26 mol/glucose unit) is dissolved in 240 ml of water, to this is added a solution comprising 160 ml of water having dissolved therein 45.4 g of ferric chloride hexahydrate and 21.6 g of ferrous chloride tetrahydrate under a nitrogen stream, and, with heating, 3N aqueous sodium hydroxide solution is added under stirring up to pH 11. Then, hydrochloric acid is added to adjust the pH to 7.0, and the mixture is refluxed with heating for 1 hour. After cooling, centrifugation is made at 2,100×g for 30 minutes, methanol is added to the supernatant up to 46% to precipitate a complex, the resultant precipitate is dissolved in water, and the solution is dialyzed against flowing water for 16 hours. The dialyzed solution is adjusted to pH 8.0 with sodium hydroxide, concentrated under reduced pressure, and filtered with a membrane filter (pore size: 0.45 μm) to obtain 249 ml of a desired complex aqueous sol (Reference example 7). Iron concentration: 56 mg/ml, particle size of the magnetic iron oxide: 7.3 nm, particle size of the whole: 73 nm, polysaccharide/iron weight ratio: 2.11, magnetization in 1 tesla: 85 emu/1 g iron, $T_2$ relaxivity: 130 $(mM.sec)^{-1}$, divalent iron rate in the whole iron: 19%.

Reference Example 8

162 g of CDX having an intrinsic viscosity of 0.050 dl/g is dissolved in 1080 ml of water, to this is added 353 ml of 3N aqueous sodium hydroxide solution, and, with heating, an aqueous solution comprising 222 ml of 1M aqueous ferric chloride solution (corresponding to 60.0 g of ferric chloride hexahydrate) having dissolved therein 21.6 g of ferrous chloride tetrahydrate under a nitrogen stream. Then, 6N hydrochloric acid is added to adjust the pH to 7.0, and the mixture is refluxed with heating for 1 hour and 30 minutes. After cooling, the same treatment as in Reference example 1 is carried out to obtain 160 ml of a desired complex aqueous sol (Reference example 8). Iron concentration: 55 mg/ml, particle size of the magnetic iron oxide: 4.5 nm, particle size of the whole: 36 nm, polysaccharide/iron weight ratio: 1.08, magnetization in 1 tesla: 73 emu/1 g iron, $T_2$ relaxivity: 68 $(mM.sec)^{-1}$, divalent iron rate in the whole iron: 13%.

Comparative Example 1

4 ml of 1M citric acid solution is added to 200 ml of the complex aqueous sol of CDX having an intrinsic viscosity of 0.050 dl/g with the oxidized magnetic iron oxide (iron concentration: 56 mg/ml) prepared according to Reference example 4, the pH is adjusted to 8 with 3N aqueous sodium hydroxide solution, the mixture is stirred for 10 minutes and filtered with a membrane filter (pore size: 0.2 μm), and the filtrate is autoclaved at 121° C. for 20 minutes to obtain 210 ml of a desired complex aqueous sol (Comparative example 1). Iron concentration: 54 mg/ml, particle size of the magnetic iron oxide: 8.3 nm, particle size of the whole: 60 nm, polysaccharide/iron weight ratio: 1.00, magnetization in 1 tesla: 85 emu/1 g iron, $T_2$ relaxivity: 200 $(mM.sec)^{-1}$, divalent iron rate in the whole iron: 5.7%.

Comparative Example 2

10 ml of 0.4M citric acid solution adjusted to pH 8 with aqueous sodium hydroxide solution is added to 100 ml of the complex aqueous sol of CDX having an intrinsic viscosity of 0.050 dl/g with the oxidized magnetic iron oxide (iron concentration: 56 mg/ml) prepared according to Reference example 4, the mixture is stirred for 10 minutes, the pH is adjusted to 8 with 3N aqueous sodium hydroxide solution, the total volume is made to be 200 ml with addition of water, filtration is carried out with a membrane filter (pore size: 0.2 μm), and the filtrate is autoclaved at 121° C. for 20 minutes to obtain 200 ml of a desired complex aqueous sol (Comparative example 2). Iron concentration: 29 mg/ml, particle size of the magnetic iron oxide: 8.4 nm, particle size of the whole: 60 nm, polysaccharide/iron weight ratio: 1.03, magnetization in 1 tesla: 85 emu/1 g iron, $T_2$ relaxivity: 215 $(mM.sec)^{-1}$, divalent iron rate in the whole iron: 5.1%.

Comparative Example 3

To 500 ml of 16% ammonia water having dissolved therein 250 g of dextran having an intrinsic viscosity of 0.075 dl/g is gradually added with vigorous stirring over a period of five minutes 500 ml of a solution containing 75.5 g of ferric chloride hexahydrate and 32 g of ferrous chloride tetrahydrate. The slurry formed is subjected to ultrasonic pulverization (30 minutes), heated (100° C., 10 minutes), cooled, and centrifuged at 1,000×g for 20 minutes. The supernatant is diluted with water to 2 l, and concentrated to 500 ml by ultrafiltration (fractional molecular weight: 100,000 daltons). 1.6 l of water is added to the concentrate, and the mixture is concentrated up to 500 ml. This operation of water addition and concentration is repeated five times in total, 500 ml of 1M sodium citrate solution is added to the resultant concentrate, and the mixture is dialyzed for 16 hours against 10 mM of ammonium citrate buffer adjusted to pH 8.2 with ammonia water. The dialyzed solution is concentrated to 120 ml by ultrafiltration (fractional molecular weight: 100,000 daltons), and filtered with a membrane filter (pore size: 0.2 μm), and the filtrate is autoclaved at 121° C. for 30 minutes to obtain 115 ml of a desired complex aqueous sol (Comparative example 3). Iron concentration: 57 mg/ml, particle size of the magnetic iron oxide: 8.1 nm, particle size of the whole: 220 nm, polysaccharide/iron weight ratio: 0.36, magnetization in 1 tesla: 83 emu/1 g iron, $T_2$ relaxivity: 255 $(mM.sec)^{-1}$, divalent iron rate in the whole iron: 6.5%.

EXAMPLE 1

2 ml of 1M L-lactic acid solution is added to 100 ml of the complex aqueous sol of CDX having an intrinsic viscosity of 0.050 dl/g with the magnetic iron oxide (iron concentration: 57 mg/ml) prepared according to Reference example 2, and the mixture is treated in the same manner as in Comparative example 1 to obtain 103 ml of a desired composition (Example 1). Iron concentration: 55 mg/ml, particle size of the magnetic iron oxide: 8.8 nm, particle size of the whole: 81 nm, polysaccharide/iron weight ratio: 1.01, magnetization in 1 tesla: 89 emu/1 g iron, $T_2$ relaxivity: 270 $(mM.sec)^{-1}$, divalent iron rate in the whole iron: 24%.

EXAMPLE 2

1, 2 and 4 ml portions of 1M L-lactic acid solution, and 4 and 8 ml portions of 2M L-lactic acid solution are added to 200 ml portions of the complex aqueous sol of CDX having an intrinsic viscosity of 0.050 dl/g with the oxidized magnetic iron oxide (iron concentration: 56 mg/ml) prepared according to Reference example 4, respectively, and the mixtures are treated in the same manner as in Example 1, respectively to obtain about 200 ml each of desired compositions (Examples 2-1∼5).

TABLE 1

| Composition No. | Iron concentration mg/mL | Particle size nm Core part | Particle size nm whole | Weight ratio CDX/iron | Magnetization in 1 tesla emu/1g iron | $T_2$ relaxivity $(mM.sec)^{-1}$ | Divalent iron rate $Fe^{2+}$/whole iron % |
|---|---|---|---|---|---|---|---|
| 2-1 | 55 | 8.6 | 64 | 1.02 | 87 | 220 | 5.5 |
| 2-2 | 55 | 8.4 | 62 | 1.04 | 89 | 225 | 6.4 |
| 2-3 | 54 | 8.5 | 62 | 1.03 | 86 | 225 | 5.6 |
| 2-4 | 54 | 8.5 | 62 | 1.04 | 85 | 230 | 5.5 |
| 2-5 | 53 | 8.3 | 62 | 1.03 | 87 | 230 | 5.1 |

EXAMPLE 3

4 ml of 1M L-lactic acid solution adjusted to pH 8 with aqueous sodium hydroxide solution is added to 200 ml of the complex aqueous sol of CDX having an intrinsic viscosity of 0.050 dl/g with the oxidized magnetic iron oxide (iron concentration: 56 mg/ml) prepared according to Reference example 4, and the mixture is treated in the same manner as in Comparative example 2 to obtain 205 ml of a desired composition (Example 3). Iron concentration: 54 mg/ml, particle size of the magnetic iron oxide: 8.6 nm, particle size of the whole: 63 nm, polysaccharide/iron weight ratio: 1.00, magnetization in 1 tesla: 88 emu/1 g iron, $T_2$ relaxivity: 210 $(mM.sec)^{-1}$, divalent iron rate in the whole iron: 5.5%.

EXAMPLE 4

2 ml of 2M L-lactic acid solution is added to 100 ml of the complex aqueous sol of dextran having an intrinsic viscosity of 0.051 dl/g with the magnetic iron oxide (iron concentration: 56 mg/ml) prepared according to Reference example 1, and the mixture is treated in the same manner as in Example 1 to obtain 103 ml of a desired composition (Example 4). Iron concentration: 54 mg/ml, particle size of the magnetic iron oxide: 6.2 nm, particle size of the whole: 83 nm, polysaccharide/iron weight ratio: 0.61, magnetization in 1 tesla: 63 emu/1 g iron, $T_2$ relaxivity: 140 $(mM.sec)^{-1}$, divalent iron rate in the whole iron: 15%.

EXAMPLE 5

4 ml each of 0.5M solutions of monocarboxylic acids or monocarboxylic acid water soluble salts are added respectively to 50 ml portions of the complex aqueous sol of CDX having an intrinsic viscosity of 0.050 dl/g with the oxidized magnetic iron oxide (iron concentration: 56 mg/ml) prepared according to Reference example 4, and the mixtures are stirred for 10 minutes, adjusted to pH 8 with aqueous sodium hydroxide solution, made to 100 ml with addition of water, filtered with a membrane filter (pore size: 0.2 μm), and autoclaved at 121° C. for 20 minutes, respectively, to obtain 100 ml of desired compositions (Examples 5-1~6). Any of the resultant preparations does not exhibit a hypotensive action.

85 emu/1 g iron, $T_2$ relaxivity: 245 $(mM.sec)^{-1}$, divalent iron rate in the whole iron: 3.5%.

EXAMPLE 7

1.5 ml of 1M L-lactic acid solution is added to 100 ml of the complex aqueous sol of CDX having an intrinsic viscosity of 0.120 dl/g with the zinc ferrite (iron concentration: 42 mg/ml, zinc concentration: 16 mg/ml) prepared according to Reference example 6, and the mixture is treated in the same manner as in Comparative example 1 to obtain 102 ml of a desired composition (Example 7). Iron concentration: 40 mg/ml, zinc concentration: 15 mg/ml, particle size of the magnetic metal: 10.1 nm, particle size of the whole: 110 nm, polysaccharide/metal weight ratio: 1.31, magnetization in 1 tesla: 29 emu/1 g metal, $T_2$ relaxivity: 25 $(mM.sec)^{-1}$.

EXAMPLE 8

2 ml of 1M L-lactic acid solution is added to 100 ml of the complex aqueous sol of carboxymethylated dextran having an intrinsic viscosity of 0.115 dl/g and a substitution degree of 0.26 mol/glucose unit with the magnetic iron oxide (iron concentration: 56 mg/ml) prepared according to Reference example 7, and the mixture is treated in the same manner as in Comparative example 1 to obtain 103 ml of a desired composition (Example 8). Iron concentration: 54 mg/ml, particle size of the magnetic iron oxide: 7.4 nm, particle size of the whole: 70 nm, polysaccharide/iron weight ratio: 2.11, magnetization in 1 tesla: 83 emu/1 g iron, $T_2$ relaxivity: 140 $(mM.sec)^{-1}$, divalent iron rate in the whole iron: 15%.

EXAMPLE 9

2 ml of 1M L-lactic acid solution is added to 100 ml of the complex aqueous sol of CDX having an intrinsic viscosity of 0.050 dl/g with the magnetic iron oxide (iron concentration: 55 mg/ml) prepared according to Reference example 8, and the mixture is treated in the same manner as in Example 1 to obtain 100 ml of a desired composition (Example 9). Iron concentration: 54 mg/ml, particle size of the magnetic iron oxide: 4.5 nm, particle size of the whole: 39 nm, polysaccharide/iron weight ratio: 1.07, magnetization in 1 tesla: 74 emu/1 g iron, $T_2$ relaxivity: 70 $(mM.sec)^{-1}$, divalent iron rate in the whoie iron: 9.3%.

TABLE 2

| Composition No. | Iron concentration mg/mL | Particle size nm Core part | Particle size nm whole | Weight ratio CDX/iron | Magnetization in 1 tesla emu/1g iron | $T_2$ relaxivity $(mM.sec)^{-1}$ | Carboxylic acid used |
|---|---|---|---|---|---|---|---|
| 5-1 | 28 | 8.6 | 63 | 1.03 | 89 | 230 | Acetic acid |
| 5-2 | 28 | 8.3 | 63 | 1.03 | 88 | 230 | 4-Hydroxy-n-butyric acid |
| 5-3 | 28 | 8.7 | 63 | 1.06 | 85 | 195 | Glycolic acid |
| 5-4 | 28 | 8.5 | 60 | 1.08 | 84 | 215 | Gluconic acid |
| 5-5 | 28 | 8.5 | 63 | 1.05 | 87 | 230 | 4-Amino-n-butyric acid |
| 5-6 | 28 | 8.6 | 67 | 1.04 | 86 | 225 | L-glutamic acid |

EXAMPLE 6

2 ml of 1M L-lactic acid solution is added to 100 ml of the complex aqueous sol of CDX having an intrinsic viscosity of 0.120 dl/g with the oxidized magnetic iron oxide (iron concentration: 55 mg/ml) prepared according to Reference example 5, and the mixture is treated in the same manner as in Comparative example 1 to obtain 103 ml of a desired composition (Example 6). Iron concentration: 51 mg/ml, particle size of the magnetic iron oxide: 7.7 nm, particle size of the whole: 93 nm, polysaccharide/iron weight ratio: 0.97, magnetization in 1 tesla:

EXAMPLE 10

4.5 ml of 1M L-lactic acid and 7.8 g of mannitol are added to 100 ml of the composition obtained in Reference example 4 (iron concentration: 56 mg/ml), 3N sodium hydroxide solution is added to make the pH 9, and then, water is added to make the total volume 224 ml (iron concentration: 25 mg/ml). While filtration is carried out with a membrane filter (pore size: 0.2 μm), 3 ml portions of the mixture are poured into ampoules, nitrogen is filled into the ampoules, and the contents are autoclave sterilized at 121° C. for 20 minutes, respectively, to obtain a desired complex aqueous sol preparation (Example 10). This preparation is usable as a MRI contrast agent.

EXAMPLE 11

11 ml of 1M phosphate buffer is added to 100 ml of the composition obtained in Example 2-5 (iron concentration: 53 mg/ml), 3N sodium hydroxide solution is added to make the pH 7, and then, water is added to make the total volume 530 ml (iron concentration: 10 mg/ml). While filtration is carried out with a membrane filter (pore size: 0.2 μm), 10 ml portions of the mixture are poured into sterilized vials, respectively, to obtain a desired complex aqueous sol preparation. This preparation is usable as a MRI contrast agent.

EXAMPLE 12

4.3 g of dextran 40 is added to 100 ml of the composition obtained in Example 2-4 (iron concentration: 54 mg/ml), 3N sodium hydroxide solution is added to make the pH 7, and then, water is added to make the total volume 216 ml (iron concentration: 25 mg/ml). While filtration is carried out with a membrane filter (pore size: 0.2 μm), 4 ml portions of the mixture are poured into sterilized vials respectively, freeze-drying is carried out, and argon gas is filled thereinto to obtain a desired complex powder preparation. This preparation can be used as a MRI contrast agent by dissolving it in physiological saline at the time of use.

EXAMPLE 13

110 g of hydroxpropylcellulose is added to 100 ml of the composition obtained in Example 1 (iron concentration: 55 mg/ml), 3N sodium hydroxide solution is added to make the pH 7, and then water is added to make the total volume 5,500 ml (iron concentration: 1 mg/ml). While filtration is carried out with a membrane filter (pore size: 0.45 μm), 100 ml portions of the mixture are poured into sterilized plastic vessels, respectively, to obtain a desired complex aqueous sol preparation. This preparation can be used as a MRI contrast agent orally administered.

Test Example 1

Effects on platelet number were investigated, respectively by the complex aqueous sols prepared in the reference examples, comparative examples and examples described above. Blood for control was taken from each of rabbits weighing 2 to 3 kg, and the test solutions were intravenously administered to the animals, respectively, in a quantity of 5 mg metal(s)/0.5 ml/kg each. Blood was taken from each of the animals 5 minutes thereafter, EDTA was added thereto, 101-fold dilution was made with 1% ammonium oxalate solution, the resultant dilution was put in a hemocytometer, and platelet number was measured by a phase-contrast microscope (Brecher & Cronkite method). The results are shown in Table 3.

Text Example 2

Acute toxicities ($LD_{50}$) were determined, respectively of the complex aqueous sols prepared in the reference examples, comparative examples and examples described above. 5, 10, 20, 40 and 80 mmol/kg portions in terms of metal(s) of each complex aqueous sol were intravenously administered to groups of five-week-old dd-strain mice (male), each group consisting of 5 animals, respectively, their life or death was observed for 2 weeks, and then $LD_{50}$ values were calculated by the Litchfield & Wilcoxon method. The $LD_{50}$ values of the complex aqueous sols are shown in Table 4.

TABLE 3

| Complex aqueous sol No. | Acid concentration nM/1M iron | Residual Platelet % |
| --- | --- | --- |
| Reference example 1 | — | 5 |
| Reference example 2 | — | 3 |
| Reference example 3 | — | 4 |
| Reference example 4 | — | 56 |
| Reference example 5 | — | 56 |
| Reference example 6 | — | 8 |
| Reference example 7 | — | 4 |
| Reference example 8 | — | 36 |
| Comparative example 1 | 20 | 97 |
| Comparative example 2 | 40 | 76 |
| Comparative example 3 | 30 | 11 |
| Example 1 | 20 | 38 |
| Example 2-1 | 5 | 76 |
| Example 2-2 | 10 | 84 |
| Example 2-3 | 20 | 102 |
| Example 2-4 | 40 | 109 |
| Example 2-5 | 80 | 75 |
| Example 3 | 20 | 91 |
| Example 4 | 40 | 22 |
| Example 5-1 | 20 | 91 |
| Example 5-2 | 20 | 103 |
| Example 5-3 | 20 | 97 |
| Example 5-4 | 20 | 82 |
| Example 5-5 | 20 | 101 |
| Example 5-6 | 20 | 70 |
| Example 6 | 20 | 76 |
| Example 7* | 20 | 32 |
| Example 8 | 20 | 19 |
| Example 9 | 20 | 93 |
| Example 10 | 40 | 98 |
| Example 11 | 80 | 103 |
| Example 12 | 40 | 99 |

*The acid concentration in Example 7 is mm/1M metal total concentration.

TABLE 4

| Complex aqueous sol No. | $LD_{50}$ mmol iron/kg |
| --- | --- |
| Reference example 1 | 20 |
| Reference example 2 | 23 |
| Reference example 3 | 20 |
| Reference example 4 | 22 |
| Reference example 5 | 30 |
| Reference example 6 | 32 |
| Reference example 7 | >80 |
| Reference example 8 | 40 |
| Comparative example 1 | 9 |
| Comparative example 2 | 7 |
| Comparative example 3 | 5 |
| Example 1 | 23 |
| Example 2-1 | 21 |
| Example 2-2 | 29 |
| Example 2-3 | 28 |
| Example 2-4 | 22 |
| Example 2-5 | 21 |
| Example 3 | 20 |
| Example 4 | 18 |
| Example 5-1 | 20 |
| Example 5-2 | 24 |
| Example 5-3 | 20 |
| Example 5-4 | 21 |
| Example 5-5 | 25 |
| Example 5-6 | 23 |
| Example 6 | 30 |
| Example 7* | 30 |
| Example 8 | >80 |
| Example 9 | 36 |
| Example 10 | 23 |
| Example 11 | 18 |
| Example 12 | 21 |

*The complex aqueous sol concentration in Example 7 is mmol metals/kg.

Test Example 3

In vivo MR images were photographed using the complex aqueous sol preparation prepared in Example 10. Namely, 20 μmol/kg portions in terms of metal(s) of this preparation were intravenously administered to Wistarstrain rats having implanted Novikoff tumor in the liver, respectively, photographs were made by a spin-echo method at a repeat time of 400 msec and an echo time of 25 msec, using a MRI apparatus for animals produced by Sisco Co. (California, USA), to obtain MR images at the liver sites. These images are shown in FIGS. (A), (B), (C) and (D). (A) and (B) in FIG. 1 are MR images before the administration of this preparation and (C) and (D) in FIG. 1 are MR images at 60 minutes after the administration of this preparation.

Test Example 4

Histopathologic examination of lungs was made by administering to animals both complex aqueous sols prepared in Comparative example 1 and Example 2-3. Namely, 5 mmol/kg portions in terms of metal(s) of each complex aqueous sol were intravenously administered to groups of five-week-old dd-strain mice (male), each group consisting of 5 animals, respectively, autopsy was made 5 minutes thereafter and the lungs were extirpated, tissular preparations were prepared, Berlin blue staining was made, and the resultant preparations were observed by a light microscope.

In the group to which the complex aqueous sol of Comparative example 1 was administered, emboli were observed in the lung of each mouse. A photomicrograph of an example among them is shown in FIG. 2 (A). On the other hand, in the group to which the complex aqueous sol of Example 2-3 was administered, no embolus was observed in the lung of any mouse. A photomicrograph of an example among them is shown in FIG. 2 (B).

In addition, the same test as in the case of the mice was carried out on Hartley-strain guinea pigs (male) and Japanese white rabbits (female and male), and similar results were obtained.

Industrial Applicability

As is described above, the magnetic metal oxide ultrafine particles-containing composition of this invention, which has no side effects such as platelet aggregation, is excellent in safety to living bodies, and has no bad influence on living bodies even when intravascularly administered, and thus, is useful in fields such as medicine and diagnostic drugs, particularly as an MRI contrast agent.

We claim:

1. A composition containing magnetic metal oxide ultrafine particles, which comprises
   (A) an aqueous sol of a complex of the magnetic metal oxide ultrafine particles with at least one polysaccharide derivative selected from the group consisting of carboxy polysaccharides and carboxyalkyl ethers of polysaccharides; and
   (B) a water-soluble monocarboxylic acid having no more than 10 carbon atoms.

2. The composition of claim 1 wherein the magnetic metal oxide is represented by the formula $$(M^{II}O)_1 \cdot M_2^{III}O_3 \quad (I)$$

wherein $M^{II}$ represents a divalent metal atom, $M^{III}$ represents a trivalent metal atom and l is a number in the range of $0 \leq l \leq 1$.

3. The composition of claim 2 wherein the magnetic metal oxide is a magnetic iron oxide wherein $M^{II}$ in the formula (I) is divalent iron and $M^{III}$ is trivalent iron.

4. The composition of claim 3 wherein the divalent iron content of the magnetic iron oxide is 10 weight % or less of the whole iron in terms of iron metal.

5. The composition of claim 1 wherein the average particle size of the magnetic metal oxide ultrafine particles is in the range of about 2 to about 30 nm.

6. The composition of claim 1 wherein the complex has a particle diameter in the range of about 10 to about 500 nm.

7. The composition of claim 1 wherein the magnetization in 1 tesla of the complex is in the range of about 10 to about 150 emu per g of the metal.

8. The composition of claim 1 wherein the complex is substantially superparamagnetic.

9. The complex of claim 1 wherein the complex has a $T_2$ relaxivity in the range of about 5 to about 1,000 $(sec.mM)^{-1}$.

10. The composition of claim 1 wherein the organic monocarboxylic acid is one containing hydroxyl group(s).

11. The composition of claim 1 wherein the organic monocarboxylic acid is one containing amino group(s).

12. The composition of claim 1 wherein the organic monocarboxylic acid is a lower aliphatic monocarboxylic acid optionally having hydroxyl group(s) or amino group(s).

13. The composition of claim 1 wherein the organic monocarboxylic acid is lactic acid.

14. The composition of claim 1 which contains the organic monocarboxylic acid in a quantity in the range of about 1 mmol to about 30 mol per mol of the metal(s) in the complex.

15. The composition of claim 1 which has a pH in the range of about 4 to about 11.

16. The composition of claim 1 wherein the polysaccharide derivative is selected from the group consisting of alkali-modified or carboxy lower alkyl-etherified derivatives of dextran, starch and pullulan.

17. The composition of claim 1, wherein the polysaccharide derivative has an intrinsic viscosity of about 0.02 to about 0.5 dl/g.

18. The composition of claim 1, wherein the complex contains the polysaccharide derivative in a quantity of about 0.1 to about 5 weight parts per weight of the metal(s) in the magnetic metal oxide.

19. The composition of claim 1, wherein the organic monocarboxylic acid has no more than 5 carbon atoms.

20. An MRI contrast composition which comprises
   (A) an aqueous sol of a complex of magnetic metal oxide ultrafine particles having an average particle diameter of about 2 to about 30 nm with at least one polysaccharide derivative selected from the group consisting of carboxy polysaccharides and carboxyalkyl ethers of polysaccharides, said polysaccharide derivative having an intrinsic viscosity of about 0.02 to about 0.5 dl/g; and
   (B) a water-soluble monocarboxylic acid having no more than 10 carbon atoms.

21. A method for diagnosing a lesion which comprises administering the composition of claim 20 to a human being or animal and making MRI contrast photographs of the reticuloendothelial system of the human being or animal.

* * * * *